(12) United States Patent
Schryver

(10) Patent No.: US 8,388,912 B2
(45) Date of Patent: Mar. 5, 2013

(54) TEMPERATURE TRANSFER DEVICES

(75) Inventor: Brian Schryver, Redwood City, CA (US)

(73) Assignee: Biocision, LLC, Mill Valley, CA (US)

( * ) Notice: Subject to any disclaimer, the term of this patent is extended or adjusted under 35 U.S.C. 154(b) by 1067 days.

(21) Appl. No.: 12/252,333

(22) Filed: Oct. 15, 2008

(65) Prior Publication Data

US 2009/0258407 A1   Oct. 15, 2009

Related U.S. Application Data

(60) Provisional application No. 60/980,167, filed on Oct. 15, 2007.

(51) Int. Cl.
*B01L 9/00* (2006.01)
(52) U.S. Cl. ......... 422/560; 422/561; 422/563; 422/566
(58) Field of Classification Search ............ 422/64, 422/129, 130, 138, 547, 552, 553, 560, 561, 422/563, 566; 436/47, 48, 157; 435/288.4, 435/303.1, 305.2, 305.3; 219/428, 429
See application file for complete search history.

(56) References Cited

U.S. PATENT DOCUMENTS

| | | | | |
|---|---|---|---|---|
| 5,616,301 | A  * | 4/1997 | Moser et al. | 422/64 |
| 6,767,512 | B1 * | 7/2004 | Lurz et al. | 422/552 |
| 6,906,292 | B2 * | 6/2005 | Weinfield et al. | 219/428 |
| 7,309,603 | B2 * | 12/2007 | Ma et al. | 435/288.3 |

* cited by examiner

*Primary Examiner* — Jill Warden
*Assistant Examiner* — Dwayne K Handy
(74) *Attorney, Agent, or Firm* — David R. Conklin; Kirton McConkie

(57) ABSTRACT

A portable temperature transfer device for transferring thermo energy to and/or from a laboratory culture plate is provided as well as its methods of use. The temperature transfer device comprises a base and a raised stage that comprises a thermal conductive material. The raised stage allows direct contact between individual wells of the laboratory culture plate and the temperature transfer device.

9 Claims, 4 Drawing Sheets

TEMPERATURE TRANSFER DEVICES

CROSS-REFERENCE TO RELATED APPLICATIONS

This application claims the priority benefit of U.S. Provisional Application No. 60/980,167, filed Oct. 15, 2007, which is incorporated herein by reference in its entirety.

FIELD OF THE INVENTION

The invention relates to temperature transfer devices and methods for using the same. In particular, some aspects of the temperature transfer devices are adapted to be used with various laboratory or cell culture plates.

BACKGROUND OF THE INVENTION

In vitro culture of a cell or tissue (hereinafter simply "cell") requires maintaining proper conditions such as temperature and humidity. In research or laboratory settings, often laboratory or cell culture plates (hereinafter simply "laboratory culture plates") are used. The laboratory culture plates generally comprise a plurality of wells that are designed to hold cells and culture medium. Typically a cell is placed in a culture fluid in a floating stateor fixed to an inside surface, or contained within a gel in which an ingredient of the culture fluid is added. Alternatively, the cell is transplanted in a material such as a matrix, a scaffold, a carrier or a mold. The cells are then allowed to proliferate and grow within the laboratory culture plates under proper conditions.

While laboratory culture wells are useful in holding individual cells and culture mediums separate from other wells, the overall design of laboratory culture plates makes it difficult to control the temperature. To control the cell culture temperature, typically the entire laboratory culture plate is placed in a temperature controlled environment such as an incubator, oven, a refrigerator, a freezer or a container filled with ice. Thus, conventional methods for controlling the temperature of laboratory culture plates requires a relatively large apparatus compared to the size of laboratory culture plates for temperature control. Furthermore, these temperature control devices are generally not readily portable nor are these methods very quick or easy to conduct in a sterile environment (e.g. under a laboratory hood).

Therefore, there is a need for a laboratory culture plate temperature control device that is portable and/or relatively small.

SUMMARY OF THE INVENTION

One aspect of the invention provides a portable temperature transfer device for transferring thermal energy to and from a laboratory culture plate. Generally the laboratory culture plates comprise a plurality of wells. Often these laboratory culture plates are commercially available in 8, 24, 64, 96, or 384 well configurations. However, it should be appreciated that the scope of the invention is not limited to temperature transfer devices that are configured to be used with any particular number of wells in the laboratory culture plates.

The portable temperature transfer device typically comprises:

a base; and a stage located on top of said base, wherein said stage comprises a thermo conductive material adapted for rapidly transferring thermo energy from the temperature control device to the plurality of laboratory culture plate wells, and wherein said stage is adapted to be in contact with at least the bottom surface of the laboratory culture plate wells when the laboratory culture plate is placed on top of said portable temperature transfer device.

Typically, the stage is adapted to be operatively connected to a temperature control device.

In some embodiments, the thermo conductive material comprises a thermo conductive metal. Within these embodiments, in some instances the thermo conductive metal comprises aluminum, copper, aluminum alloy, copper alloy, or a combination thereof.

Yet in other embodiments, the stage further comprises a plurality of concavities. Each concavity is generally adapted to fit at least a portion of individual laboratory culture plate well, or protrusions from the plate bottom surface. In this manner at least a portion of the side-walls of the wells are also in contact with the portable temperature transfer device. Often such configuration allows faster and/or better thermo energy transfer to/from the laboratory culture well.

Still in other embodiments, the temperature control device comprises a temperature control system for controlling the temperature of said stage.

In other embodiments, the temperature control device comprises a timer control system.

Yet still in other embodiments, the temperature control device comprises a central processing unit.

In other embodiments, the temperature control device comprises a programmable unit for automatically adjusting the temperature setting, time setting, or a combination thereof of the stage.

In some embodiments, the temperature control device is removably attached to the temperature transfer device.

Yet in other embodiments, the base comprises a thermo conductive material.

Still yet in other embodiments, the area dimension of the stage is substantially identical to the area dimension of the bottom of the laboratory culture plate. In this manner, when the laboratory culture plate is placed on top of the stage, the stage prevents any significant lateral movement of the laboratory culture plate relative to the base.

Another aspect of the invention provides a method for adjusting temperature of a laboratory culture plate, which comprises a plurality of wells. The method generally comprises:

placing the laboratory culture plate on a portable temperature transfer device, wherein the portable temperature transfer device comprises:

a base; and a stage located on top of the base and is adapted to be operatively connected to a temperature control device, wherein the stage comprises a thermo conductive material adapted for rapidly transferring thermo energy to and from the temperature control device to the plurality of laboratory culture plate wells, and wherein the stage is adapted to be in contact with at least the bottom surface of each of the laboratory culture plate wells when the laboratory culture plate is placed on top of the portable temperature transfer device; and adjusting the temperature of the laboratory culture plate wells by controlling the temperature of the stage using the temperature control device.

In some embodiments, the temperature control device is removably attached to the temperature transfer device.

Yet in other embodiments, the temperature control device comprises a heating element, a cooling element, or a combination thereof.

Still in other embodiments, the temperature of the stage is controlled prior to placing the laboratory culture plate on the portable temperature transfer device.

Another aspect of the invention provides a method for culturing cells, said method comprising:

placing the cell on at least one of the wells of a laboratory culture plate comprising a plurality of wells, wherein the well further comprises a culture medium;

placing the laboratory culture plate on a portable temperature transfer device, wherein the portable temperature transfer device comprises:

a base; and a stage located on top of the base and is adapted to be operatively connected to a temperature control device, wherein the stage comprises a thermo conductive material adapted for rapidly transferring thermo energy to and from the temperature control device to the plurality of laboratory culture plate wells, and wherein the stage is adapted to be in contact with at least the bottom surface of each of the laboratory culture plate well when the laboratory culture plate is placed on top of the portable temperature transfer device; and culturing the cells by adjusting the temperature of the laboratory culture plate wells by controlling the temperature of the stage using the temperature control device.

In some embodiments, the temperature of the stage is adjusted and the temperature transfer device is used as a stand alone heat reservoir or heat sink.

DETAILED DESCRIPTION OF THE INVENTION

The present invention will be described with regard to the accompanying drawings which assist in illustrating various features of the invention. In this regard, the present invention generally relates to temperature transfer devices. That is, the invention relates to portable temperature transfer devices for use with laboratory culture plates.

Some of the features of the temperature transfer device of the invention are generally illustrated in FIGS. 1A-1F, and 2, which are provided for the purpose of illustrating the practice of the invention and which do not constitute limitations on the scope thereof.

As used herein, the terms "laboratory culture plates" and "cell culture plates" are generally used interchangeably, unless the context requires otherwise, to refer to various commercially available multi-welled plates that are adapted for use in culturing cells or tissues. Laboratory culture plates are commercially readily available from various sources including Fisher Scientific, Sigma, Aldrich, as well as other laboratory equipment suppliers.

Referring to FIGS. 1A-1F, the temperature transfer device 100 generally comprises a base 104 and a stage 108. The stage 108 can be a raised portion of base 104 or it can be a separate add-on to base 104.

Figure 1A:
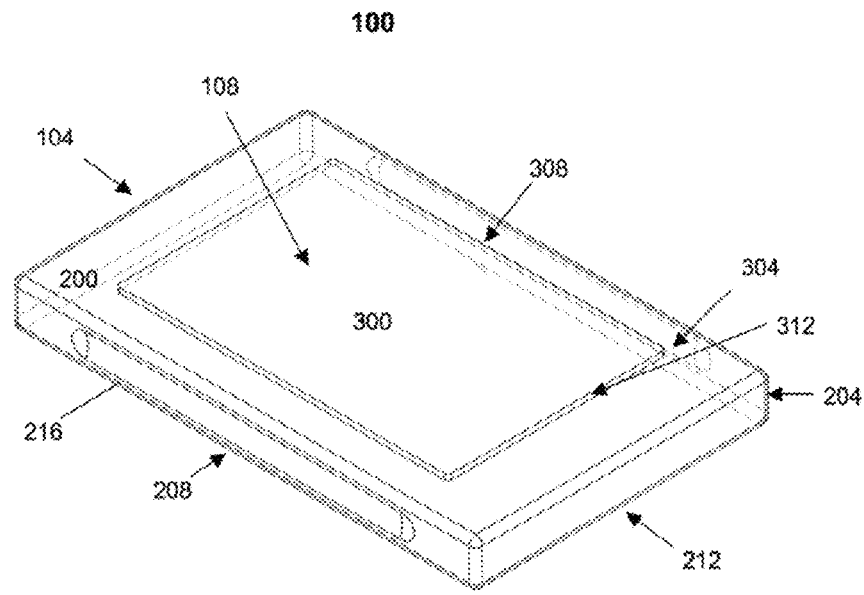
FIGS. 1A to 1F are schematic drawings of some of the various embodiments of the temperature transfer devices of the invention and the corresponding dimensions.

The top surface 200 of base 104 has height 204, width 208, and length 212. These dimensions are generally about 9 cm to about 18 cm, often about 1 cm to about 5 cm, more than the dimension of stage 108. It should be appreciated that the overall dimension of the temperature transfer device 100 is not limited to these ranges or specific ranges disclosed herein. In general, the base dimension can vary significantly based on the particular application and place of use. The base 104 can comprise a flat bottom surface 216 as illustrated in FIG. 1A, or it could comprise legs (not shown) similar to that of a typical table. However, it should be appreciated that the bottom surface 216 can be configured and designed in any manner as long as the bottom surface 216 provides a leveled stage 108.

Figure 1B:
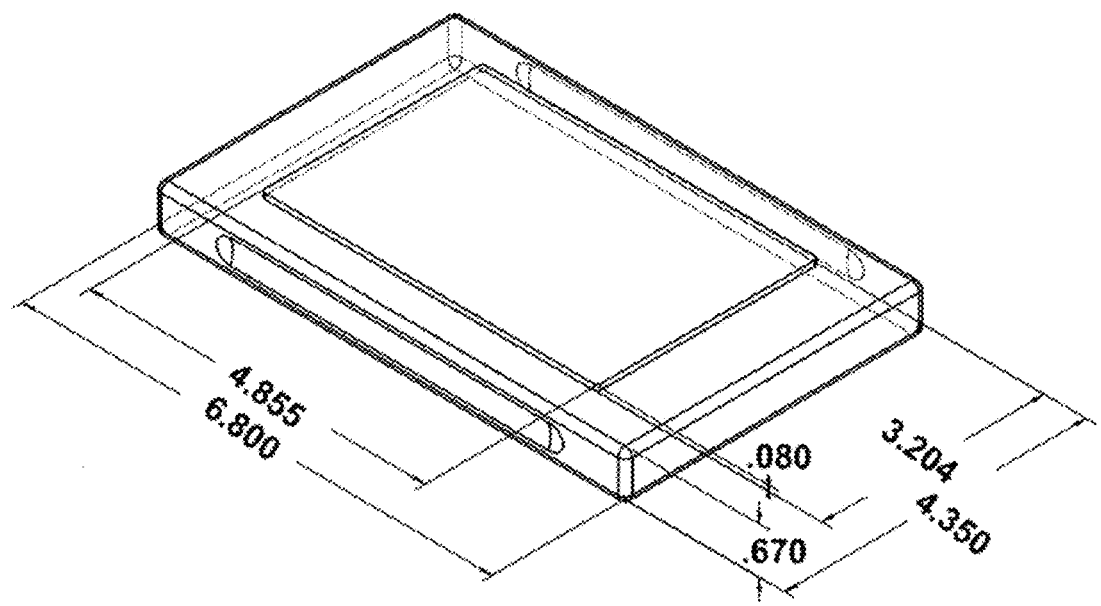
Figure 1C:
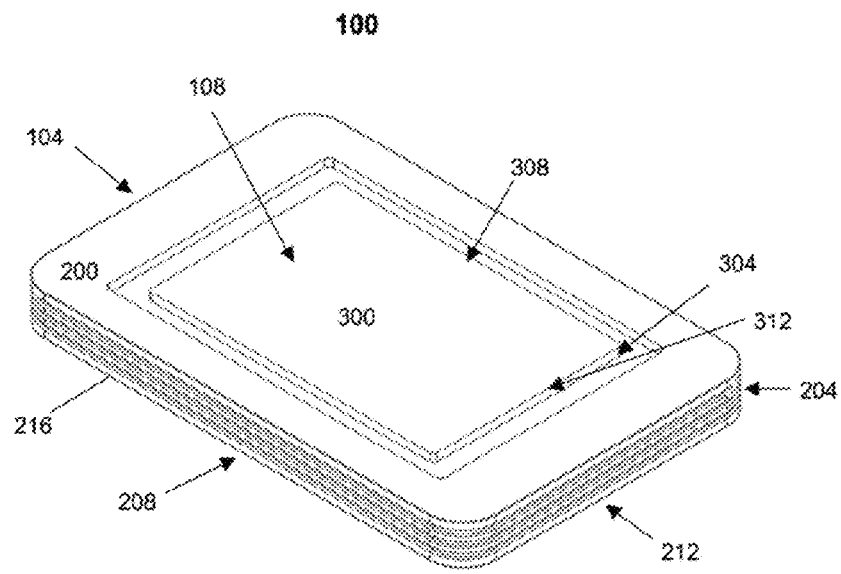
Figure 1D:
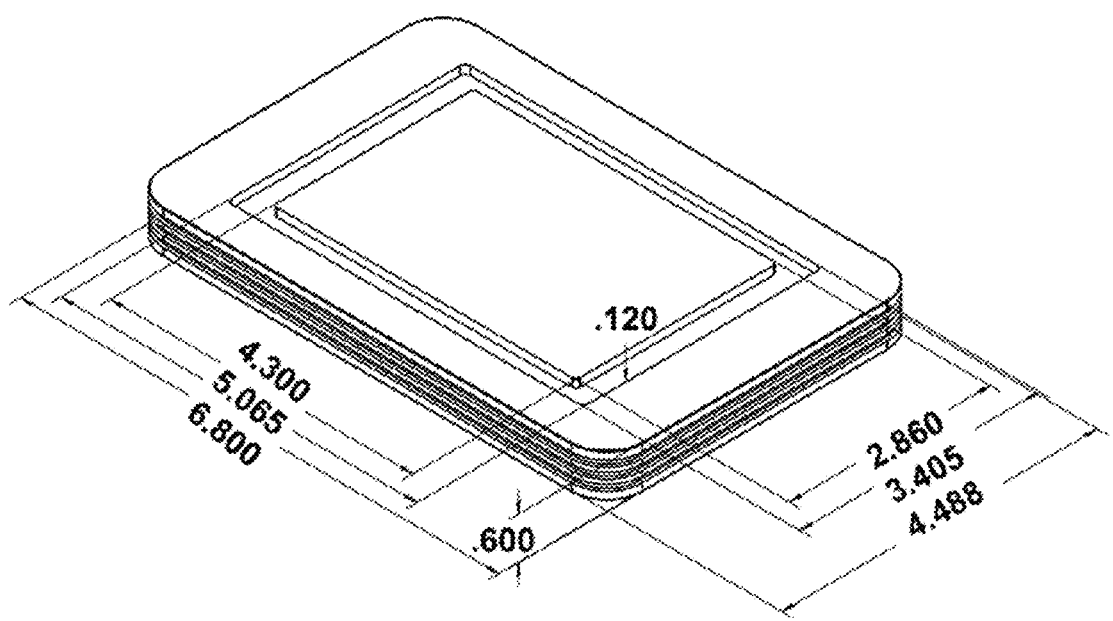

The top surface 300 of stage 108 has height 304, width 308, and length 312. These dimensions are generally determined by the dimensions of the laboratory culture plate. FIGS. 1B, 1D and 1F show temperature transfer device of the invention with some particular dimensions.

Referring again to the drawings, it can be seen that stage 108 is typically designed to fit snuggly with the laboratory culture plate so that when coupled, stage 108 restricts or prevents any substantial lateral movement of the laboratory culture plate 400. The minimum height 304 of stage 108 is also often dictated by the amount of height needed to allow the top surface 300 to be in contact with the bottom of the wells of laboratory culture plate 400.

Thus, unlike a completely flat heat sink surface which leaves an insulating air gap between the well bottom of the laboratory culture plate and the heat sink surface, the raised stage design of the temperature transfer device of the invention provides a direct contact with the well bottom of the laboratory culture plate. The raised stage of the temperature transfer device has an added advantage of restricting or preventing lateral movement of the laboratory culture plate during its use, e.g., the laboratory process. The material from which the temperature transfer device is constructed allows rapid heat exchange so that the desired temperature range can be quickly established by contact with a thermal mass such as ice, dry ice, liquid nitrogen or any other cooling device, a water bath or a hot plate or any other heating device.

Figure 1E:
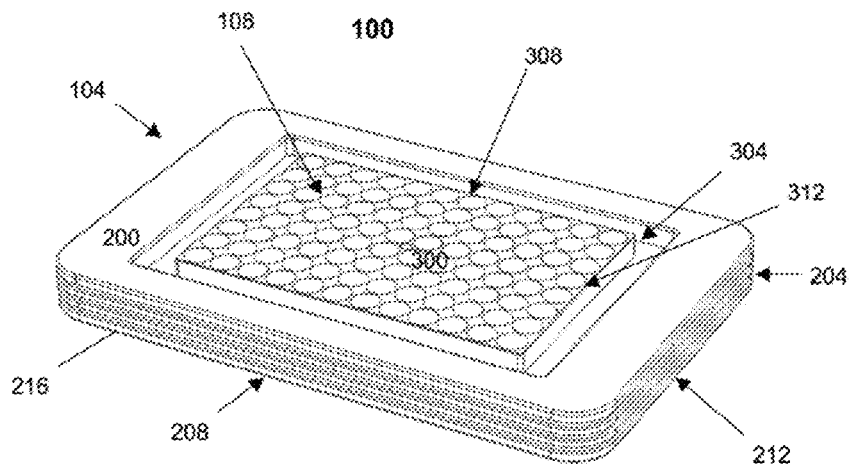
Figure 1F:
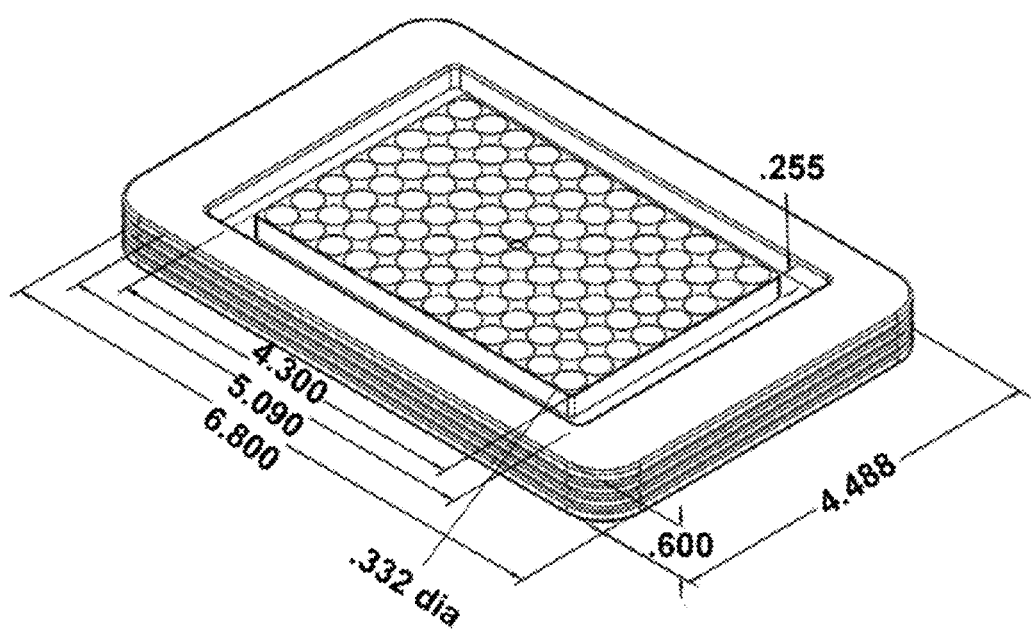
Figure 2:
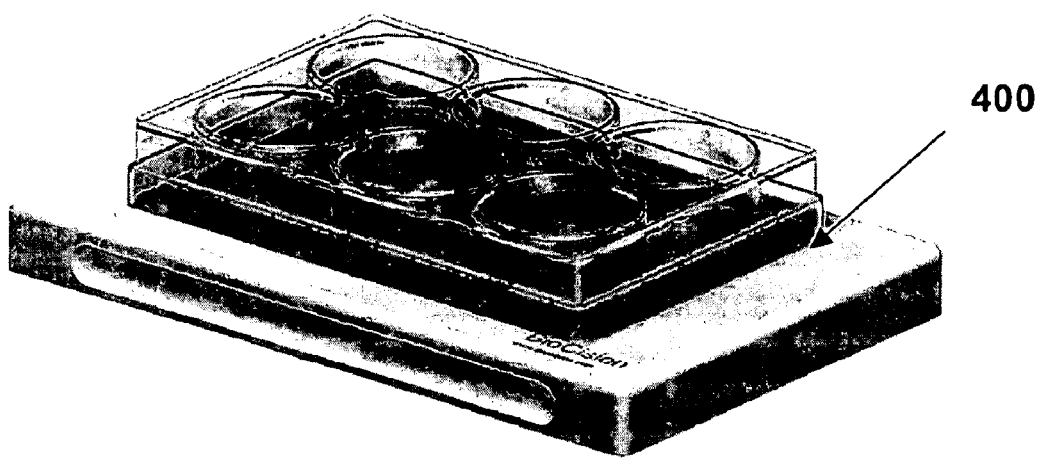
FIG. 2 is an illustration showing a laboratory culture plate on top of the temperature transfer device of the invention.

In some embodiments, the top surface 300 of stage 108 can comprise a plurality of concavity (drawn as small circles in FIGS. 1E and 1F) such that the individual wells of laboratory culture plate sits within the concavity (FIGS. 1E and 1F). Generally, the depth of concavity is such that at least a portion of the side-walls of the laboratory culture plate fits within the concavity. As can be appreciated, the more surface area contact between individual wells of the laboratory culture plate and the stage (via its concavity (FIGS. 1E and 1F) and/or top surface 300) will lead to faster heat transfer.

The stage 108 is comprised of a thermo conductive material such as aluminum, aluminum alloy, copper, copper alloy, and other materials (both metal and non-metal) that are known to be good thermo conductors. Typically, the thermal conductivity of the stage 108 that transfers thermal energy to/from a laboratory culture plate is at least about 100 W/(m*K), typically at least about 170 W/(m*K), and often at least about 170 W/(m*K). And as stated above, the temperature transfer device 100 is designed with a raised stage 108 upon which the laboratory culture plate 400 rests. The raised stage design anchors any laboratory culture plate and allows the bottom of the laboratory culture plate 400 to be in direct contact with the temperature transfer device. This design allows rapid heat transfer between the laboratory culture plate 400 and the temperature transfer device 100 while preventing any substantial lateral movement of the laboratory culture plate 400 during use.

In some embodiments, the temperature transfer device 100 is operatively connected, often the stage 108, to a temperature control device (not shown). The temperature control device can comprise an electrical device (not shown), a coil (not shown), or any other devices or means that can rapidly cool or heat the stage 108. When coil is used, it can be placed on the bottom surface of stage 108, i.e., underneath stage 108 such that the coil does not come in direct contact with the laboratory culture plate. Any temperature control coils that can heat or cool, which are well known in the art, can be used as long as the temperature of coil can be transferred to stage 108.

The temperature control device can also comprise a temperature control system, timer control system, or a combination thereof. Such systems allow one to set the desired temperature and/or time to allow automated operation. In some instances, a central processing unit (e.g., a computer) can be used as the control system(s). Both the temperature control system and timer control system are well known in the art and can be configured to be used with the temperature control device.

In some embodiments, the temperature control device is an ice-bath, ice, dry ice, liquid nitrogen, or other cold solids or liquids. Often these non-electronic temperature control devices are placed underneath the temperature transfer device 100 such that any moisture it creates is contained within the environment enclosed by the base 104. In this manner, temperature transfer device 100 prevents or substantially reduces any undesired humidity from reaching the individual wells of laboratory culture plates.

In some embodiments, as shown in FIGS. 1C-1F, the temperature transfer device 100 can also include a recessed surface along the perimeter of stage 108. Such recessed surface is typically adapted to accommodate a wide variety of different laboratory culture plates. In addition, the temperature transfer device 100 can also include a flange of top surface surrounding the recessed surface. Such a flange can also aid in securely holding a laboratory culture plate in place as well as providing a grip.

Utility

Temperature transfer device of the invention can be used for any application in which it is desired to rapidly cool or warm the contents (e.g. cell culture) of a laboratory culture plate (e.g. 96, 48, 24, 12 or 6 well plate) and substantially maintain the temperature for extended periods of time. The temperature transfer device can be used in applications that depend upon temperature stabilization of, or rapid heat transfer to or from laboratory culture plates.

As an example, mammalian cell agar assays depend on rapid cooling of a cell suspension in molten agar so that the agar solidifies before the cells have a time to settle. In this particular application, the temperature transfer device is cooled to a desired temperature and the laboratory culture plate is placed on top of the stage such that the top surface of the stage comes in direct contact with the bottom of individual wells of the laboratory culture plate. This allows the contents of the individual wells to be cooled such that the agar solidifies before the cells have a time to settle.

In some embodiments, sequence involves chilling the plate on the temperature transfer device, then adding the cells in warm liquid agar to the wells so that the suspension rapidly looses heat.

Typically, the temperature transfer device of the invention is placed on ice, dry ice, liquid nitrogen or any heating or cooling device until the temperature of the temperature transfer device has reached the approximate temperature of the cooling or heating medium. The temperature transfer device can be left in contact with the cooling or heating medium or placed on a thermally insulating surface such as plastic foam board or rubber mat. Alternatively, the temperature transfer device can have attached insulating feet. The bottom of the laboratory culture plate is then placed in contact with the pedestal stage (i.e., top surface) of the temperature transfer device. The laboratory or cell culture plate are rapidly cooled or warmed and held at equilibrium temperature without permanent physical change to the laboratory culture plate material.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed:

1. A portable temperature transfer device for rapidly transferring thermal energy to and from a laboratory culture plate comprising a plurality of wells, said portable temperature transfer device comprising:
   a base having a flat bottom surface, said bottom surface having a first width and a first length and said base further comprising a raised portion that forms a stage, such that the top surface of the stage is the top surface of the base, said top surface having a height and a second length and a second width, the second length and width being less than the first length and width, thereby creating a recessed surface interposed between the bottom of the base and the top of the raised stage;
   wherein said height of said stage is such that the top surface of the stage contacts the bottoms of the wells of said laboratory culture plate when said plate is placed on said stage; and
   wherein said portable temperature transfer device comprises a thermo conductive material adapted for rapidly transferring thermo energy from a temperature control device to the plurality of laboratory culture plate wells.

2. The portable temperature transfer device of claim 1, wherein said thermo conductive material comprises a thermo conductive metal.

3. The portable temperature transfer device of claim 2, wherein said thermo conductive metal comprises aluminum, copper, aluminum alloy, copper alloy, or a combination thereof.

4. The portable temperature transfer device of claim 1, wherein said top surface of the stage further comprises a plurality of concavities, and wherein each concavity is adapted to fit at least an exterior portion of an individual laboratory culture plate well.

5. The portable temperature transfer device of claim 1, wherein the temperature control device is selected from the group consisting of ice, dry ice, and liquid nitrogen.

6. The portable temperature transfer device of claim 1, wherein an area dimension of the stage is substantially identical to an internal area dimension of a skirt portion of the laboratory culture plate such that when the laboratory culture plate is placed on top of the stage, the stage prevents any significant lateral movement of the laboratory culture plate.

7. A method for controlling temperature of a laboratory culture plate comprising a plurality of wells, said method comprising:
placing the laboratory culture plate on a portable temperature transfer device, wherein the portable temperature transfer device comprises:
a base having a flat bottom surface, said bottom surface having a first width and a first length, and said base further comprising a raised portion that forms a stage, such that the top surface of the stage is the top surface of the base, said top surface having a height and a second length and a second width, the second length and width being less than the first length and width, thereby creating a recessed surface interposed between the bottom of the base and the top of the raised stage, wherein said height of said stage is such that the top surface of the stage contacts the bottoms of the wells of said laboratory culture plate when said plate is placed on said stage, and wherein the stage comprises a thermo conductive material adapted for rapidly transferring thermo energy to and from the temperature control device to the plurality of laboratory culture plate wells; and
placing the laboratory culture plate on the portable temperature transfer device such that the top surface of the stage contacts at least the bottom of the laboratory culture plate wells; and
placing the portable temperature transfer device into contact with a temperature control device.

8. The method of claim 7, wherein the temperature control device is selected from the group consisting of ice, dry ice, and liquid nitrogen.

9. The method of claim 7, further comprising a step for pre-cooling the portable temperature transfer device prior to placing the laboratory culture plate onto the portable temperature transfer device.

* * * * *